(12) United States Patent
Stefanchik et al.

(10) Patent No.: US 6,766,328 B2
(45) Date of Patent: Jul. 20, 2004

(54) SYSTEM FOR THE CREATION OF DATABASE AND STRUCTURED INFORMATION FROM VERBAL INPUT

(75) Inventors: Michael F. Stefanchik, Fort Collins, CO (US); John G. Mathe, Fort Collins, CO (US); Robin L. Scott, Pinson, AL (US); Steven W. Loper, Woodridge, IL (US); Christopher S. Krueger, Louisville, CO (US); Robert H. Groves, Greeley, CO (US)

(73) Assignee: Ascriptus, Inc., Greeley, CO (US)

( * ) Notice: Subject to any disclaimer, the term of this patent is extended or adjusted under 35 U.S.C. 154(b) by 0 days.

(21) Appl. No.: 10/275,194
(22) PCT Filed: Nov. 6, 2001
(86) PCT No.: PCT/US01/51026
§ 371 (c)(1),
(2), (4) Date: Oct. 31, 2002
(87) PCT Pub. No.: WO02/46886
PCT Pub. Date: Jun. 13, 2002

(65) Prior Publication Data
US 2004/0030704 A1 Feb. 12, 2004

Related U.S. Application Data
(60) Provisional application No. 60/246,328, filed on Nov. 7, 2000, provisional application No. 60/246,329, filed on Nov. 7, 2000, and provisional application No. 60/246,381, filed on Nov. 7, 2000.

(51) Int. Cl.[7] ............................................... B06F 17/30
(52) U.S. Cl. .................. 707/101; 707/10; 707/104; 704/2; 704/8; 704/9; 704/201; 704/205; 704/277
(58) Field of Search ................................. 704/277, 275, 704/9, 235, 2, 8, 201, 205, 500, 214, 231; 84/603, 613, 622, 659; 713/186; 707/3, 102, 4, 101, 10, 100; 709/218, 227

(56) References Cited

U.S. PATENT DOCUMENTS 5,689,585 A  * 11/1997  Bloomberg et al. .......... 382/229
5,704,371 A     1/1998  Shepard ...................... 128/897

(List continued on next page.)

FOREIGN PATENT DOCUMENTS

WO    WO 02/46886 A2   6/2002

OTHER PUBLICATIONS

PCT Exam Report for PCT/US01/51026 mailed on Jul. 18, 2002, 5 pages.

PCT Search Report for PCT/US01/51026 mailed on Jun. 14, 2002, 5 pages.

*Primary Examiner*—Jean M. Corrielus
(74) *Attorney, Agent, or Firm*—Santangelo Law Offices, P.C.

(57) ABSTRACT

A system through which verbal information can be utilized to create structured data with tags or inserted codes such as an XML code or the like provides hand held capability for easy adoption via CE, cell telephone, or other data entry devices. A visual display at the time of dictation can provide checklists, prompts or otherwise shape the entry to comport to a selected data context. The visual display can also be part of a transcriptionist system. By providing data in a coded fashion, analysis can be easily conducted such that alerts, bioterror alerts (e.g. evolving symptom or trend information for anthrax or the like) can be rapidly and perhaps automatically identified, and acted upon such as in providing health care alerts or locationally oriented statistical analysis information. A central database reporting function to a central authority (e.g., to the CDC or law enforcement) can be included for terrorist and other event management.

196 Claims, 2 Drawing Sheets

U.S. PATENT DOCUMENTS

| | | | |
|---|---|---|---|
| 5,822,544 A * | 10/1998 | Chaco et al. | 705/2 |
| 6,026,363 A | 2/2000 | Shepard | 705/3 |
| 6,172,948 B1 * | 1/2001 | Keller et al. | 369/83 |
| 6,272,575 B1 * | 8/2001 | Rajchel | 710/301 |
| 6,362,409 B1 * | 3/2002 | Gadre | 84/603 |
| 6,405,195 B1 * | 6/2002 | Ahlberg | 707/4 |
| 6,556,973 B1 * | 4/2003 | Lewin | 704/277 |
| 6,615,350 B1 * | 9/2003 | Schell et al. | 713/168 |
| 2002/0099534 A1 * | 7/2002 | Hegarty | 704/2 |
| 2003/0046073 A1 * | 3/2003 | Mori et al. | 704/251 |

* cited by examiner

SYSTEM FOR THE CREATION OF DATABASE AND STRUCTURED INFORMATION FROM VERBAL INPUT

TECHNICAL FIELD

Generally, this invention relates to a computer-based system for transcription and related information and other security and data intensive information or the like. Specifically, the invention may focus on applications, methods, software, hardware, services, and even business methods which can provide a variety of functions important in transcribing or handling information, such as medical information, including but not limited to convenient transcription with menu data tailoring as may be of interest to some of the users of the particular information involved. It may involve handling the information through a network such as the global information network or Internet. Specifically, the invention focuses on applications, methods, software, hardware, services, and even business methods which can provide a variety of functions important in the handling of the information, including but not limited to access, research, and other such functions. It can provide a variety of functions important in the dealing with the information, including but not limited to encoding such information with details of interest to some of the users of such information.

BACKGROUND

One of the more inefficient environments in which to capture data is that from verbal information. Because verbal or perhaps dictated information can use a variety of words or phrases for a singular meaning and because verbal information can be highly originator dependent, it can be challenging to capture in a structured data format. But one example is that of the medical environment. This environment can present not only one for which the need can be acute (such as to help the patient with a potentially fatal complication) but also one in which the structures and formats can range from one of insurance billing to one of a need for immediate correlation of information. This is compounded by the professional not having the time to enter the data manually. Moreover, the threat of bioterrorism has become the reality of a bioterrorist attack. Although the technology used to attack was quite simple, the consequences of the ensuing terror have been far reaching and profound. It has become vividly clear that attacks cannot be entirely prevented. Our best weapon then, is in the rapid collection and sharing of critical information and responding to bioterrorist attacks, a process that is entirely dependent on rapid, accurate and comprehensive data capture.

In but one application, it can be understood that healthcare in general and physician practices in particular, have not kept abreast of dramatic improvements in the technology of data capture and management. As a direct result, all stake holders from patient to providers are suffering. Technology solutions have not been adopted by the vast majority of physicians, who for the most part, function as independent small groups focused on patient interaction and patient care, and have little time or patience with high tech solutions. It is, however, quite clear that this is a fragmented market and a giant of a market waiting breathlessly for a palatable solution.

In the medical example, physicians are sometimes quoted as losing money at the rate of up to $60,000 per physician per year because of the complexity of a reimbursement system that literally forces them to choose from millions of possible coding combinations in order to get paid. Driving the revenue loss is the stern gaze of the government and the threat of monetary and even criminal penalties should physicians err on the side of over-charging for their services. Incomplete fragments of patient information are literally hidden in inaccessible paper files in hospital and physician practices around the country and tens of millions of dollars are wasted annually in trying to manage this paper nightmare. The need for a solution is staggering, and yet no one has yet solved this puzzle. Why? The answer lies in a deep understanding of physician practice mechanics and physician culture. Doctors know they have a problem and are indeed in pain. But the pain of the solutions offered have to date been greater than the pain of the existing problem.

The scope of the problem can be understood by realizing that physicians represent merely one type of service provider that is impossibly busy. In many industries, the service provider sees patients or clients non-stop from the time they arrive at their offices until the time they go home. Sixty hour weeks are the norm and their focus during that time is the patient or client; relating to the patient or client, evaluating the patient or client, determining the patient's or client's problems, offering a possible solution, implementing a plan, and explaining this plan with reassurance to the patient or client. In short, the practice of medicine as many other services is very much a relational, interpretive and interpersonal affair. The art of medicine is at least as important as the science which is applied. After each emotionally demanding and intellectually challenging encounter, the physician then must document his thoughts, impression and plan, and justify his reasoning in a legal document. With more patients stacking up to be seen, there is precious little time to accomplish this task, so the vast majority of physicians must dictate the results of the encounter, often very rapidly, with no time left to edit or review before the next patient encounter. Physicians do not, will not, cannot learn new methods of data entry that are less flexible and more time consuming. This is why today, less than 5% use any sort of electronic medical record. Keyboards, pen charts and inaccurate, unedited voice recognition programs cannot serve their needs and so they rely on an existing transcription system and somewhat haphazard coding solution to help them document and justify each encounter. Physicians are willing to pay for this service and pay well to relieve them of the burden of learning a new career, i.e., documentation and coding. They are people oriented, not technology oriented and can and will pay to have someone else manage this aspect of healthcare. Many have mistakenly assumed that if they build a data repository and provide the physicians with a screen and keyboard or a drop list and pen chart, that physicians will flock to them in droves. Many such technologically advanced solutions exist now, and in large part they have been ignored or quickly abandoned. The threshold of entry is simply too great.

The provider will require service as part of the data capture solution. Technology alone is not enough. Furthermore, doctors as well as others often want local service. Someone they or their staff can personally call and hold accountable. Someone who does not hide behind the veil of bureaucracy, but who is available and at risk in the relationship. In the medical application, today, the local medical transcriptionist fills that roll for creating edited paper documents. Mirroring the healthcare industry, medical transcriptionists are also typically small, fragmented, but local accountable shops which serve physician needs. They too, have a need. They realize that eventually technology will replace them, and yet they don't know when. They realize that their clients, the doctors, needs are only partially served by the paper documents that they, the transcriptionist provide. Their very careers are at stake, but because they are small and fragmented, they do not have the individual resources to solve doctor's problems alone. Likewise, coding solutions are many, varied and fragmented and likewise, though they are aware of physician suffering; professional coders don't have the insight or resources to comprehensively address the need.

In the context of sharing information, one of the problems appears to be the fact that healthcare in general and physician practices in particular have not kept abreast of dramatic improvements in the technology of data capture and management. The primary disconnect in our public health surveillance system remains the archaic system of data sharing between and among public health facilities, and as importantly between the public health system and private practicing physician as well as the private system of hospitals and clinics. In September, 1999, the Senate Appropriations Committee requested, and subsequently received a status report on public health's infrastructure. One of the primary needs identified in this document is the need for robust information and data systems. As a result of that report, the Health Alert Network became a key priority of both the Centers for Disease Control, and the Secretary of the Department of Health and Human Services. The HAN was designed to meet the goals and recommendations set by the status report. One of three primary goals identified is as follows:

"Goal number 2, robust information and data systems GOAL: Each health department will be able to electronically access and distribute up-to-date public health information and emergency health alerts, monitoring the health of communities, and assist in the detection of an emerging public health problem.

Recommendation 5: By 2010, ensure that all health departments have continuous high speed access to the internet and standard protocols for data collection, transport, electronic reporting and information exchange that protects privacy and seamlessly connect local, state, and federal data systems.

Recommendation 6: By 2010, ensure that all health departments have immediate online access to current public health recommendations, health and medical data, treatment guidelines and information on the effectiveness of public health interventions.

Recommendation 7: By 2010, ensure that all health departments have the capacity to send and receive sensitive health information via secure electronic systems and to broadcast emergency health alerts among hospitals, medical centers, universities, and local public health systems and agencies."

As to the medical application, clearly, these goals must be achieved to successfully leverage currently available technology and protect the public health. The events of September 2001 however, make it equally clear that a fragmented state-by-state approach may get us there by 2010, but we no longer enjoy the luxury of time. There is now an immediate and tangible threat that must be addressed in months, not years. Furthermore, a key component in the electronic chain has not been adequately addressed by these important recommendations or by the health alert network. Namely, successful, accurate data capture by providers in the field, both public and private. Unfortunately, technology solutions have not been adopted by the vast majority of physicians who, for the most part, function independently. They are focused on patient interaction and patient care, and keeping abreast of the rapid evolution of medical knowledge and have had little time or patience for high tech solutions. As a result, incomplete fragments of patient information are buried in inaccessible paper files in hospital and physician practices around the country. Not only are tens of millions of dollars wasted in trying to manage this paper nightmare, but literally billions of dollars are lost due to our inability to capture the data and glean critical information on public health, treatment efficacy and the early detection of health trends so that effective and rapid solutions can be deployed. If the information cannot be captured, it cannot be managed. If it cannot be managed, then care cannot be optimally improved. This simple logic has profound implications for responsiveness to bioterrorist threats as well as the overall public health and safety.

SUMMARY OF THE INVENTION

Conceptually, the invention can be presented and understood from a variety of perspectives. With the understanding that such details are not limiting, from one perspective it can be understood by reference to four device-oriented aspects: a CE or other personal computing capability recorder object, a functionality for precision coding through software and applications or the like, a separate CE or other personal computing capability such as an active-synch docking portal station, and even file transfer protocols such as, in a medical application for example, a health insurance portability and accountability act (HIPAA) compliant electronic signature aspect. Each of these aspects can of course be presented and used separately or they may be combined with any combination or permutation of these or other aspects to present an overall system.

From a data creation perspective, the invention can be understood as potentially encompassing a data tagging engine or other functionality, perhaps or even functionality for parsing text to data, an application for dealing with a workflow digital stream such as in one application for a medical transcriptionist or other such user, and a HIPAA compliant electronic note security transfer system. Again, each of these aspects can of course be presented and used separately or they may be combined with any combination or permutation of these or other aspects to present an overall system.

In addition, the invention can also be understood from an information flow or access perspective by reference to a digital stream, an Internet or other access database, an automated patient information services, and an interactive portal-based knowledge delivery system. One more, each of these aspects can of course be presented and used separately or they may be combined with any combination or permutation of these or other aspects to present an overall system.

One task in solving the problem is in simply capturing the data. The invention includes elements designed to tap into the vast amount of data and information that every moment in every office in America is dictated into a hand held portable tape recorder. The invention can many the two concepts of coding and a checklist by placing the custom templates directly on the screen of a hand held device such as a pocket PC. The invention can permit dictation directly "into" a pre-chosen template on a pocket PC, thus creating a digital.wav or other file of structured data that is then sent to a secure site such as via the Internet. An existing network of local independent transcriptionists can be leveraged (in many cases it may be the medical transcriptionist the doctor is already using) to access that structured data via the web and plug it into templated data fields as he or she is transcribing or editing the note. Surprisingly this can be accomplished simply and seamlessly. To the transcriptionist, it is an opportunity to provide a solution to their clients and save their careers doing much the same work they have always done, but they no longer need to drive to the site of practice, pick up tapes and because the technology can interface seamlessly with existing practice management software; they also no longer face the nightmare of matching demographic information to dictated tapes. Now the data (coding, for example) can be shaped, captured, and structured in one seamless process that leverages existing networks and does so without increasing cost to the physician or decreasing compensation to the transcriptionist. In fact, the technology can be further leveraged to save the physician or other person substantial time (through the use of customized macros), money (through more accurate coding) and to relieve the burden of fragmented, inaccessible patient data by collecting the information in a secure site accessible from any Internet portal. Further, using an XML model and leveraging semi-automation, the invention can allow an interface with existing systems. In one embodiment, wireless, portable remote hand held units can function as two-way data and information portals.

The hand held data entry device can be used to record pertinent data of any kind such as disease surveillance data, ICD-9 or CPT coding information, physical examination, history or lab data. Because the system is portable and voice driven, and because the data can be shaped and structured with templates and checklists, there is optimum flexibility and a very flat learning curve (i.e., as easy as dictating into a tape recorder with a checklist at your fingertips) and therefore, should have high adoption rates. The data can also be securely stored in a central database in XML format where it can be aggregated and then queried to serve a variety of needs. Further, the template model can allow any entity to create custom templates and checklists downloaded from the web to shape data entry such that specific critical data elements can be captured and tagged. In addition, the solution can work both ways. Not only can customized templates be deployed via the Internet to all hand held data entry devices, but they can also receive health alerts, updates and pertinent templates immediately in real time, dramatically shortening the information cycle in both directions. Remote systems with radio wireless technology can be used to keep remote sites connected to the central data processing repository and the health alert network in real time.

MODES FOR CARRYING OUT THE INVENTION

From a more general view, the invention involves systems, methods, and devices to create structured data, that is data which is in a format that it can be readily used in a particular environment. The system is designed to provide an easily used data creation process where the initial content generator need not have any specialized knowledge. It is designed to permit verbal information entry and to take that input and proceed through a process whereby an end result is a perhaps even a highly structured database (1) of information, perhaps even including embedded data tags (2) or other structure which can enable more appropriate—or more easy—use of the data. As should be easily appreciated, the invention has application to a variety of fields. Literally any field in which information is generated and is desired to be used may benefit to some degree by the various elements of the invention. In this regard, it should also be understood that although the invention will frequently be explained in the context of a medical application—itself representing a new and unique use for such new and unique techniques—such is not intended to be limiting.

Perhaps the most tangible aspect of an embodiment is the use of some type of computing device to permit verbal data entry by a user who has content contributions to make. The computing device, perhaps may be a portable computing device, such as a digital recorder or the like. It may even be a hand held data entry device (3) with somewhat limited capability. As explained below, this first computing device may even be augmented by other, more full featured devices or capabilities.

In one example, the hand held data entry device (3) may be a CE or other personal computing capability recorder object. This aspect of the invention generally relates to and may include a COM (Common Object Model) software component object perhaps written in C++ or the like and compiled as a COM object for distributed use in building applications which may require or find useful the recorder functionality. Specifically, this element of the invention may focus on and may provide for designing, for coding, and for compiling a new or other COM object that may possess the desired functionality for use in applications which may require or find useful a digital recording functionality embedded in a CE-based or other such database form.

In addition, this element of the invention may include an ability to add a recorder object into an application that has the desired functionality to start, stop, pause, or utilize a slide bar to the desired point in the record. It may serve to capture voice in a digital format (such *.wav, MP3, or otherwise) perhaps in a designer-variable but acceptable quality range. It may use an optimized CODEC to balance audio quality, digital compression ratio, and optimal size of the resulting *.wav file.

A functionality for precision coding through software and applications may be included at a variety of levels. This aspect of the invention generally relates to and may include a database form developed for Windows CE Pocket PC or other such devices. It may have embedded prompts (4), again at multiple levels, built into the pick lists that may assist the health care or other such professional or user (5) to select the optimum, accurate, and precise codes in support of the medical or other such record or data requirements. In a medical application, such coding may be specified by the American Medical Association (AMA) or other directing body. Specifically, this aspect of the invention may focus upon programming techniques and tool applications that may embed data elements and schema into CE-based or other such forms with application software code that may prompt the user to interactively enter 'elements' (aka data) and 'SUBMITS' (aka 'commit to the database'). These may act to build a coding outline for use in the dictation (e.g., voice capture to *.wav file) module.

Perhaps one of the most significant problems that this invention addresses is to put the immense coding options rule set, such as may be specified by the AMA or otherwise, into the hands of the physician or other user (5) on a mobile, portable, or even hand held device at the point of use or care where the physician or other person can choose elements for the patient exam or other event from a pick list or a check list. This may include prompts (4) and may build an interactive outline that may serve as a template to dictate into a voice-captured file stored as a *.wav format for transcription.

Figure 1:
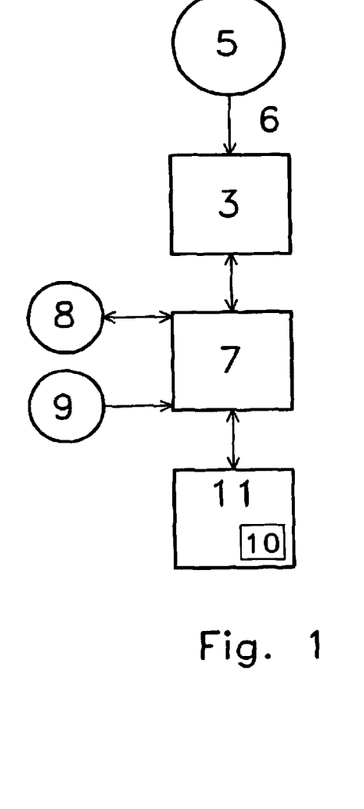
FIG. 1 is a schematic depiction of one embodiment of the invention.

Referring to FIG. 1, it can he seen that the overall system may involve several elements which each supply different functionality for the ultimate end result. In a basic form, the system may permit a user(S) to provide verbal information (6) that is captured by a first device such as the hand held data entry device (3). This hand held data entry device (3) may then accomplish some function and ten may provide and receive information from a separate computing device. This may include an inserted code transcription system (7), which may itself have a transcriptionist input element (8) whereby even more traditional transcription input can be provided. To facilitate the creation of the desired structured data, there may also be included, at some level, a tag element, such as an extensible markup language generator (9). Finally, in this embodiment, there may even be another capability for total storage, analysis, and use of aggregate information (10). This may exist at any level, including but not limited to that of a central authority (ii) or the like.

Figure 2:
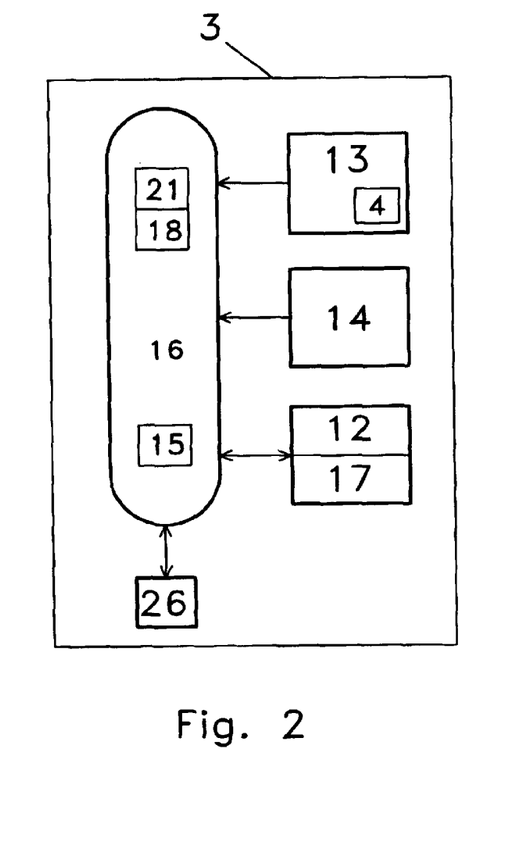
FIG. 2 is a block diagram of a portable capability in one embodiment.

A purpose of the overall system is, of course, to create structured data appropriate to a particular data context. In order to facilitate this, and as depicted in FIG. 2, embodiments may include a memory or other item which includes a stored data context element (12). This element may assist the user (5) in providing appropriate substance. It may also aid in creating structured data as explained below. To serve any of these purposes, it may be configured as a display to which the user (5) may refer during his or her creation of verbal input. This may aid in the creation of appropriate verbal information and may thus serve to assure the existence of appropriate input.

As should be understood, this can be varied greatly depending upon the particular data needs. Thus the term data context is intended to encompass any aspect which assist in the creation of an appropriate input. This can range from providing simple pick lists, to checklists, to highly specialized inputs. All that is necessary is that the element or step serve to aid in the desired creation to be considered as providing a context within which the information is utilized or generated. Perhaps a more easily understood embodiment of this general concept is the potential of using a visual display (13) as a context element. As such, it can be understood that the visual display can serve to guide the user (5). By selection of the appropriate information to provide, it may even serve as a data entry influence material display. Its information can thus serve as data entry influence material. By establishing such material as correlated to the data context, it can serve to shape the entry as desired.

There are, of course, many ways in which to correlate or coordinate the display to the data context. The context itself may be designed as a data input need context, as a data information need context, as a user reminder context, as a context designed to hold paramount the currency of information, as a statistical input need context, or even as a near real time statistical generated need context. All of this can be created using the principles of a document type definition structure. It could even act to prompt the generation of data which meets a particular document type definition. The context could provide for field segmented information, for ordering information, or even for sequencing through field segmented information.

An aspect of the invention is the possibility of making the data context information available to the user (5) at the time of verbal information generation. In one embodiment, this may be accomplished by having the data context information controlled by a first computing device, such as the hand held computing device (3). This could aid the user (5) in ordering the information verbally generated, in sequencing through appropriate data fields, or in providing the appropriate format of information. Thus, the structured data could be arranged in a field format, an ordered format, a subcontext format, a meta language format, and even an embedded code format. Importantly each of these wide ranging types of desired end result could be supported by the device at the time of dictation. The data entry influence material could be checklist material, pick list material, entry prompt information, or any other type of information as it is the resultant structured data which is desired, not the means of achieving it. Through appropriate file or screen creation, the software subroutines could serve as an entry order element, a sequenced field element, a document type definition structure element, a document type definition structure prompt, a field segmented display or any other type of element.

As mentioned earlier, this invention can be configured for a great variety of applications. Thus the data context element can be set up as a medical diagnosis information element, a patient diagnosis information element, a medical insurance information element, a exotic medical event information element (such as prompting for appropriate diagnosis of anthrax or another unusual and perhaps hard to discern event or the like), as bioweapon diagnosis information element, or otherwise.

An important feature is the invention's ability to use verbal information. An embodiment may accomplish this by converting at least a portion of the verbal input into representative data or even digital verbal data. There may be a verbal information entry element (14). This may serve as an input to a file generation element (15). The file generation element (15) may be programming, hard wiring, or read-only memory controlled capability within a first computing device's capabilities (16). It may thus exist to be accomplished on a hand held data entry device (3) or the like. As can be understood, the file generation element (15) can serve to generate any type of file from a verbal or voice input. These could range from wave files (e.g., a file having at least some *.wav structure or compatibility and thus created through a wave file generator), to MP3 files, to speech recognition files, the latter at present likely requiring too much computing capability and speed to be practical but likely becoming more practical as technology advances. Once generated, the verbal information file may be stored—at least temporarily. Storage, temporary or otherwise, may likely occur on the same hand held device at the same locations as that where the dictation occurs. This may be accomplished by providing a verbal information memory element (17) and a verbal information capture element (20) which together may serve to capture the verbal information in some form.

Even at the point of data creation it is possible to begin the process of creating actual structured data. This could be accomplished by creating the data in a tagged format from the outset. Where the first computing device's capabilities (16) are not sufficient to generate tags (as likely with present technology), the system may accept user input as an instruction to insert an appropriate tag. This input may take any form, however, in its most simplistic form it may be a key stroke or touch pad click which tells the hand held data entry device (3) that a specific item has just been or is about to be entered. Such an input could be considered a binary (that is discretely determined) user input with the input element and the related subroutine to recognize it acting as a binary input element (19). This could then insert a preliminary or other tag (2) into the stream of dictation and could serve as a structured data information insertion element (21). This could thus result in the insertion of even partial data structure information by the hand held data entry device (3). Such a tag could of course serve to aid a transcriptionist in understand the type of data about to be or just dictated. If so configured, the information stored in the verbal information memory element (17) might even be some type of composite structured data—part verbal and part inserted code with the memory serving as a hand held composite data memory. Thus the hand held data entry device (3), could include at least a first part of a structured data establishment element (18) perhaps as a partial structured data information insertion element.

As mentioned, the end result is the creation of structured data. This may be accomplished with a data tagging engine or even by parsing text to data. This aspect of the invention generally relates to and may include a set of proprietary wrappers around proprietary or industry-standard computerized meta-languages, including but not limited to SGML and it's subset XML, that may enable the creation of a medical or other note XML (Extensible Mark-up Language) schema, perhaps including DTD (Document Type Definition), and XSLT (Extensible Stylesheet Language Transformations) specifications. Specifically, this aspect of the invention may focus on shaping information from a business 'use-case' into a content-driven meta language to capture a variety of descriptive aspects for the data element of specific, detailed interest.

Perhaps one of the most significant problems that this invention may address is the functionality to shape business knowledge or other information from a variety of domains, or foci, that are typically captured as text, and potentially to create a uniform meta language that describes the data and allows for the text-based information to be parsed into data elements which may be captured in a database for storage and retrieval.

This can be accomplished by transforming the verbal information into structured data within the desired data context. Since the point-of-dictation device may have limited capability, a second computing device, perhaps a full featured computing device may be used to accomplish this more demanding function. For efficiency this may be accomplished at a second location or even on a second computing device where specialized transcriptionists are stationed. Thus the second device could include a second part of a structured data establishment element (18).

Figure 3:
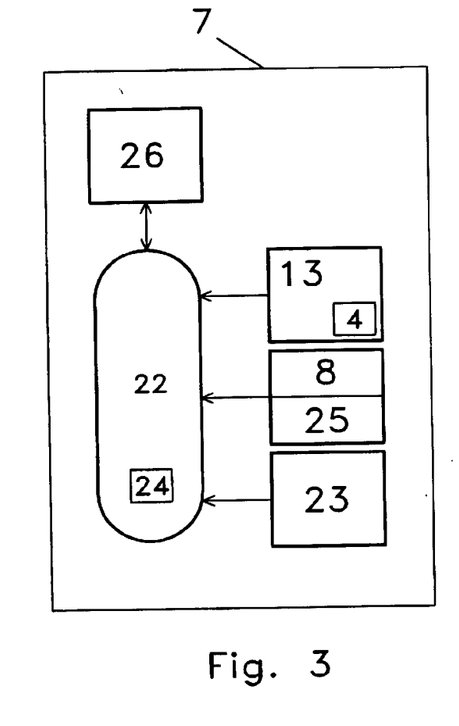
FIG. 3 is a block diagram of a transcriptionist system in one embodiment.

As mentioned earlier and as illustrated in FIG. 3, this second computing device may be configured as part of an inserted code transcription system (7), that it may be configured to facilitate or accomplish not only the conversion of verbal information into text but also an associated insertion of structured data codes or the like as well. Both the conversion to text and the insertion of codes may be accomplished automatically, manually, or by a hybrid system where a transcriptionist (such as a skilled medical transcriptionist or professional coder) is available to make the appropriate judgment or insert the appropriate codes or tags as required. This can be accomplished by providing the transcriptionist input element (8) mentioned earlier whereby transcriptionist tagging can occur. As can be appreciated, there may also be provided prompts (4) or the like in the inserted code transcription system (7) which may be triggered by analysis or by inserted codes or the like to aid the transcriptionist. All this may be controlled by the second computing device's capabilities (22) such that the system acts to establish tagged structured data within the data context or to establish structured data in a tagged format.

Figure 5:
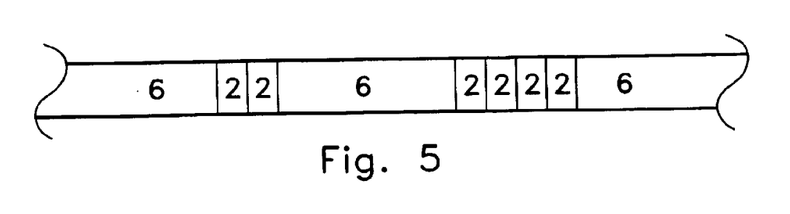
FIG. 5 is a conceptual depiction of a tagged structured data in one embodiment.

Once fully created, this element may create the structured data; this may be stored in a structured data memory (23). By appropriate design, the system may provide for the creation of structured data for a particular data context. As such the system may serve as or include a data context configured structured data establishment element (24). When configured for the input of particular tags or codes which are tailored to the appropriate data context the system may serve as or include a data context configured tagged structured data establishment element. For accountability or original data retention, the system may include in the structured data original unaltered verbal information which may be stored in a unaltered verbal information storage element. As depicted in FIG. 5, this could result in including at least a portion of the digital verbal data originally captured within the structured data.

The system could be configured to create multiple structured data formats as well. This might be helpful for various jurisdictional requirements (insurance, CDC, etc.) and might result in the inclusion of a multiple data structure establishment element such as an appropriate subroutine or otherwise. For compatibility, a common coding format such as extensible markup language (XML) format could be used. By proper design or programming, the software or hardware might provide a tagged data input (25), perhaps such as an extensible markup language generator.

The medical or other transcriptionist may work with a workflow digital stream application or an application for dealing with a workflow digital stream. This aspect may generally relate to and may include capability directed to automating the workflow process for a digital-stream dictation environment. This may be accomplished by digital-streaming technology, databasing applications, and/or Internet access computing environments. Specifically, this aspect may focus on or provide for any of the following: for automating the workflow process for digital transcriptionists along a continuum starting with Internet to access digitized voice files in a *.wav format, for storage of the *.wav file in a database for security and distribution, for retrieval and transcription processing into a text file (*.rtf format), for storage of the text file (and .XML file counterpart) in a SQL (Structured Query Language) database or the like, and for delivery back to the client using the same, secure Internet connection at the start of the process.

In systems which utilize separate locations or which store or provide end structured data to a separate location, it can be helpful to include transfer capability. A data transfer element (26) may exist at several levels. Transfer from the hand held data entry device (3) to the inserted code transcription system (7) may be automatic and as mentioned later can be accompanied by an upload of some sort as well. For convenience, the system may be designed to facilitate a wireless manner of transfer, an Internet manner of transfer, and even a cellular telephone system based manner of transfer. Appropriate elements could be included such as a wireless transfer element, an Internet transfer element, and a cellular telephone system transfer element. This may be configured for and may serve primarily to transfer digital verbal data. Since sensitive data it may also be configured to securely transfer such data.

Transfer may also occur to/from other locations such as the inserted code transcription system, and even a central authority or repository (11) where aggregate information (10) is stored and maintained. Since medical or other data can be highly sensitive, the data transfer element (26) may include an information stripper (27) for stripping individual identity information to create individual anonymous information at a particular location. Naturally any data transfer element (26) may be designed as a secure information transfer element.

The possibility of using an active-synch docking portal station may also be included. This aspect of the invention generally relates to and may include a proprietary component system to optimize the Active-Synch functionality for Windows CE or other such devices. It may be designed to enable Healthcare or other professionals or users (5) to achieve the fastest and most secure synching process from the Pocket PC (Windows CE PDA device) or other such device to a local docking bay or connected capability for caching and data transfer. Specifically, this aspect of the invention may focus on designing and coding an optimal set of components into an application to enhance the standard functionality of ActiveSynch, thereby allowing faster, more efficient, and more secure transfer of data from a CE-based PDA (personal digital assistant) or other such device to a PC-based docking or connection station, and from the docking or other station to a secure web site for storage and audit functionality. In this regard, another significant problems that this invention addresses is to create a custom application that adds to the functionality of the standard ActiveSynch function by addressing the needs of large file transfer, speed and reliability of data transmission, efficiency of moving large voice files, security of the file transfer during transmission, and security of the file arriving at specified destinations with return receipt capabilities and audit trail documentation.

Yet another aspect of the invention which may be understood in a medical context is the HIPAA-compliant electronic note security transfer system or functionality. Generally, this aspect of the invention may relate to and provide for embedding the HIPAA (Health Insurance Portability and Accountability Act) security standards into an Internet-accessed electronic note delivery system for secure note transfer and audit trail creation. Specifically, this aspect of the invention may focus on and provide for building a secure document transfer application that utilizes any security specification, including but not limited to the most recent set of security specifications under HIPAA, such hereby incorporated by reference. All may be provided for Internet transfer and database storage of highly sensitive, patient information files when the context relates to medical information.

The invention may be configured to create a secure application environment for document transfer across the Internet. This may be based on the HIPAA or other such specifications. Configuration consistent with any mandate for all of health care to deploy the standards and an audit trail for the entire life of the document transfer may be automatically provided.

For further security, an electronic signature aspect such as the HIPAA-compliant signature requirement may be included. This aspect of the invention may include an electronic signature software application to authenticate a Healthcare or other person or professional to a secure web-site and to deliver established content to the properly authenticated user. Specifically, this aspect of the invention may focus on and provide a use of logging in through a user interface portal with a USER_NAME and PASSWORD or the like to authenticate to a secure-architecture system. While obtaining rights through appropriate permissions, it may also gather access to all authenticated allocated resources and may return a graphic image <graphic: signature> to close out <contract> the transaction. It may also be designed to accommodate and comply with electronic signature legislature specifications.

The invention may act to wrap a secure environment—and the details that describe and mandate a high level of security—around the need to accept and close out a transaction (e.g., in the medical example, closing out a medical note for permanent entry into a patient's medical record) with a necessary final step in the process, the signature of the physician or other person of record and a visually pleasing graphic signature to indicate document completion and closure.

The invention may also provide automation from 'cradle-to-grave' for a voice file's transition into a text and data file to be delivered to the client, while potentially also allowing the transcriptionist to have custom tools all along the continuum that maximize the efficiency and security of the document works-in-progress.

Figure 4:
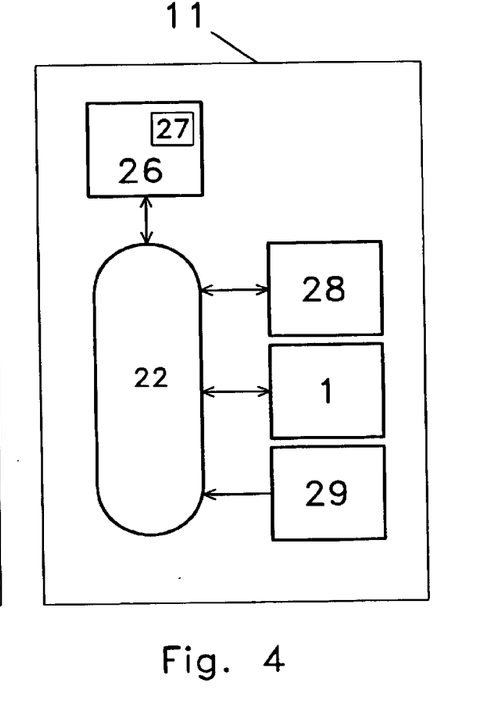
FIG. 4 is a block diagram of a central data repository in one embodiment.

Once the structured data is created, it may be utilized in a multitude of fashions. An important possibility in this regard is the possibility of providing for statistically analyzing not only the individual record, but also the aggregate information created by multiple stored structured data. Referring to FIG. 4, by compiling the various structured data into a database (1), the possibility of analyzing the database (1) and its aggregate information (10) can be understood. If, for example, the aggregate information (10) is stored in a database (1) at a central authority or repository (11), a data analysis element (28) such as a statistical analysis element or otherwise could review the data periodically or upon its entry into the database (1). By presenting an aggregated multiple stored structured data analysis element, neural network analysis element, trend analysis element, or otherwise, the system could identify impacts or risks not easily identified earlier. The techniques for analysis are, of course, varied ranging from statistical analysis, to trend analysis, to artificial intelligence analysis, to even neural network analysis. From this, the system could identify relevant information as a result of such analysis. This could include unusually frequent symptoms or events, could correlate events by location or the like. In a conflict environment it could correlate battlefield events. In the homeland it could correlate event by town, county, postal chain, by multiple postal chains, by governmental subdivision, by pre-established statistical area, or the like. It could also automatically provide information to a central authority, perhaps such as the Center for Disease Control, the Office of Homeland Security, a law enforcement agency, or even to multiple law enforcement agencies simultaneously.

Of course the system could also provide information to the user. This could be accomplished by providing an information upload element such as by making any one of the data transfer elements (26) serve in a two way capacity as shown. In this manner the system could provide relevant information such as retroactive information (relating to a prior, just analyzed record) to the user. By uploading information, it would also be possible to alert the user to a particular concern, to query the user for additional information, or even to inform the user of available information (such as information in a recommendation to change procedures for a particular event) as might be available from separate resources (29). Since the point-of-dictation device is already displaying information, it could display the potentially relevant information to the user. In the current terrorist and biological terror environment, it could also provide healthcare provider alert information, symptom identification information, and even location specific information. The visual display (13) could thus be configured as a user alert element or even a healthcare provider alert information display. For locational-dependent items, this may be facilitated by including the capability for GPS or other location data in the point-of-dictation device.

This upload of information could occur automatically or be prompted at any time such as by providing for an update of information prior to a download, prior to use of the device, or even at the time of a download. A central authority download element could be available at any time as well as a pre-utilization information upload element and a download linked information upload element.

As mentioned earlier, the entire system could be configured for a variety of applications. It could be used to generate medical diagnosis information. In this fashion it might permit the user to dictate patient diagnosis information, to dictate insurance claim information, to dictate potentially exotic medical event information, to dictate potential bioweapon symptom information, or to dictate Centers for Medicare and Medicaid Services (CMS)—secure information for later storage or analysis.

Other applications are also possible, including the possibility of configuring the system to generate law enforcement related information. Law enforcement professionals could dictate crime scene information, dictate potential terrorist event information, dictate potential bioweapon event information, dictate accident event information, or the like for similar storage and analysis.

Even general businesses could use the system by configuring it to generate business information such as in dictating business billing information, dictating service provided information, or even dictating mechanical or maintenance information. As to each of the foregoing, subroutines or hardware could be configured to serve as a law enforcement information element, a potential bioweapon event information element, or the like.

In providing the information for research or use, a digital stream, Internet access research database may be provided. This aspect may provide capabilities for a seamless, easy-to-use, front-end access interface for clinical users to gain access to their private, detail data sources and to public, summarized data sources from any browser enabled system. Specifically, it may focus on a compiled application that is a front-end graphical user interface (GUI), and a set of middleware application software functionalities that supply the business rules for front-end user selections to interact with back end data stored in a SQL (Structured Query Language) database or the like.

The invention can be designed to simplify a clinical or other user's interaction with a standard browser by enabling application functionality that may tie the user's need to query the database, with the allowable permissions, access, and usability of the data stored within the database.

Automated patient or other subject information services may also be provided. This aspect may provide capabilities for a seamless, easy-to-use, front-end access interface for patients to gain access to their private, detailed medical or other record data sources and to public, summarized data sources from any browser enabled system. Similarly to that mentioned above, this aspect may focus on or involve a compiled application that is a front-end graphical user interface (GUI), and a set of middleware application software functionalities that supply the business rules for the front-end user selections to interact with the back end data stored in a SQL (Structured Query Language) database or the like. In a medical application, the system may be designed to simplify a patient's interaction with a standard browser by enabling application functionality that ties the user's need to query the database, with the allowable permissions, access, and usability of the data stored within the database. By providing an interactive portal-based knowledge delivery system the system may provide a proprietary or other software application that may use the Internet to gather user information and requests to build and package a custom response in the form of an electronic deliverable.

A significant aspect of the invention it that it may simplify a user's interaction with a standard browser by enabling application functionality that ties the user's need to query the database, with the allowable permissions, access, and usability of the data stored within the database, and then has the database return an interactive document to customize (or shape) the content into the desired deliverable for the client.

As can be easily understood from the foregoing, the basic concepts of the present invention may be embodied in a variety of ways. It involves both computer transcription and related techniques as well as devices to accomplish the appropriate computer enhanced processes. In this application, the transcription techniques are disclosed as part of the results shown to be achieved by the various system described and as steps which are inherent to utilization. They are simply the natural result of utilizing the systems as intended and described. In addition, while some systems are disclosed, it should be understood that these not only accomplish certain methods but also can be varied in a number of ways. Importantly, as to all of the foregoing, all of these facets should be understood to be encompassed by this disclosure.

The discussion included in this provisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in process-oriented terminology, each element of the process may be implicitly performed by some device. Apparatus claims may not only be included for such devices, but also method or process claims may be included to address the functions the invention and each element performs. Neither the description nor the terminology is intended to limit the scope of the claims which will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of the step of "transcribing" should be understood to encompass disclosure of a "transcriber"—whether explicitly discussed or not—and, conversely, were there effectively disclosure of an "transcriber", such a disclosure should be understood to encompass disclosure of the step of "transcribing" and even a "means for transcribing" Such changes and alternative terms are to be understood to be explicitly included in the description.

Thus, support should be understood for any claiming of not only the listed claims, but also at least: i) each of the methods or processes as herein disclosed and described, ii) the related device to accomplish such processes, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the elements disclosed, xi) processes performed with the aid of or on a computer as described throughout the above discussion, xii) a programmable apparatus as described throughout the above discussion, xiii) a computer readable memory encoded with data or programs to direct a computer comprising means or elements which function as described throughout the above discussion, xiv) a computer configured as herein disclosed and described, xv) individual or combined subroutines and programs as herein disclosed and described, xvi) the related methods disclosed and described, xvii) similar, equivalent, and even implicit variations of each of these systems and methods, xviii) those alternative designs which accomplish each of the functions shown as are disclosed and described, xix) those alternative designs and methods which accomplish each of the functions shown as are implicit to accomplish that which is disclosed and described, xx) each feature, component, and step shown as separate and independent inventions, and xxi) the various combinations and permutations of each of the above and any element claimed or disclosed. In this regard it should be understood that for practical reasons and so as to avoid adding potentially hundreds of claims, the applicant may have presented claims with initial dependencies only.

Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

The claims set forth in this specification by are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Any acts of law, statutes, regulations, or rules mentioned in this application for patent, any patents, publications, priority documents, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, the following references are hereby appended and hereby incorporated by reference, however, as to each, to the extent that such information or statements incorporated by reference might be considered inconsistent with the patenting of this/these invention(s) such statements are expressly not to be considered as made by the applicant(s).

Finally, it should be noted that this application claims the benefit of and makes priority claims to U.S. Patent Application Nos. 60/246,328, 60/246,329, 60/246,381, filed on or about Nov. 7, 2000. Each of these applications is hereby incorporated by reference.

What is claimed is:

1. A method of creating structured medical data comprising the steps of:

a. establishing a data context within which information is utilized;

b. visually displaying data entry influence material correlated to said data context on a first computing device;

c. user generating verbal medical information which is shaped to coordinate at least some degree to said data context by said data entry influence material;

d. converting at least a portion of said verbal medical information into digital verbal data representative of at least a portion of said verbal medical information on said first computing device;

e. at least temporarily storing said digital verbal data on said first computing device;

f. transferring said digital verbal data to a second computing device; and g. transforming said digital verbal data into structured data by use of said second computing device; and h. inserting at least some data structure information with at least a portion of said verbal medical information on said first computing device to create composite structured data.

2. A method of creating structured medical data as described in claim 1 wherein said step of transforming said digital verbal data into structured data by use of said second computing device comprises the step of establishing structured data in a tagged format.

3. A method of creating structured medical data as described in claim 2 wherein said step of establishing a data context comprises the step of creating a document type definition structure.

4. A method of creating structured data comprising the steps of:

a. establishing a data context within which information is utilized;

b. visually displaying data entry influence material correlated to said data context;

c. user generating verbal information which is shaped to coordinate to at least some degree to said data context by said data entry influence material, wherein said verbal information includes business information;

d. converting at least a portion of said verbal information into digital data representative of at least a portion of said verbal information;

e. at least temporarily storing said digital verbal data; and f. transforming said digital verbal data into structured data in a meta language format within said data context.

5. A method of creating structured data as described in claim 4 wherein said step of visually displaying data entry influence material correlated to said data context comprises the step of visually displaying data entry influence material on a computing device, and wherein said step of converting at least a portion of said verbal information into digital verbal data representative of at least a portion of said verbal information comprises the step of converting at least a portion of said verbal information into digital verbal data on the same computing device.

6. A method of creating structured data as described in claim 5 wherein said steps of visually displaying data entry influence material on a computing device, and said step of converting at least a portion of said verbal information into digital verbal data on the same computing device each comprise the step of utilizing a portable computing device.

7. A method of creating structured data as described in claim 6 and further comprising the step of transferring said digital verbal data from said portable computing device to a second computing device.

8. A method of creating structured data as described in claim 7 wherein said step of transforming said digital verbal data into structured data within said data context comprises the step of utilizing said second computing device.

9. A method of creating structured data as described in claim 7 wherein said step of transferring said digital verbal data from said portable computing device to a second computing device comprises the step of transferring said digital verbal data in manner selected from a group consisting of a wireless manner of transfer, an internet manner of transfer, and a cellular telephone system based manner of transfer.

10. A method of creating structured information comprising the steps of:

a. establishing a data context within which information is utilized;

b. user generating verbal information, wherein said verbal information includes business information;

c. capturing at least a portion of said verbal information on a computing device;

d. converting at least a portion of said verbal information into digital data representative of at least a portion of said verbal information; and e. establishing structured data in a meta language format utilizing said verbal information.

11. A method of creating structured data as described in claim 10 wherein said step of establishing structured data in a tagged format utilizing said verbal information comprises the steps of:

a. converting at least a portion of said verbal information into digital verbal data representative of at least a portion of said verbal information;

b. at least temporarily storing said digital verbal data; and c. transforming said digital verbal data into structured data within said data context.

12. A method of creating structured data as described in claim 11 wherein said step of transforming said digital verbal data into structured data within said data context comprises the step of including at least a portion of said digital verbal data within said structured data.

13. A method of creating structured data as described in claim 11 wherein said step of converting at least a portion of said verbal information into digital verbal data representative of at least a portion of said verbal information comprises the step of converting at least a portion of said verbal information into digital verbal data at a first location, and wherein said step of transforming said digital verbal data into structured data within said data context comprises the step of transcriptionist taggingsaid digital verbal data at a second location.

14. A method of creating structured data as described in claim 10 and further comprising the step of visually displaying information to said user.

15. A method of creating structured data as described in claim 14 wherein said step of visually displaying information to said user comprises the step of visually displaying data entry influence material correlated to said data context to said user on a first computing device, and wherein said step of transforming said digital verbal data into structured data within said data context comprises the step of transforming said digital verbal data at a second computing device.

16. A method of creating structured data as described in claim 11 and further comprising the step of visually displaying data entry influence material correlated to said data context to said user on a first computing device, and wherein said step of transforming said digital verbal data into structured data within said data context comprises the step of transforming said digital verbal data at a second computing device.

17. A method of creating structured data as described in claim 16 wherein said step of visually displaying data entry influence material correlated to said data context to said user on a first computing device comprises the step of utilizing a portable computing device.

18. A method of creating structured data as described in claim 17 and further comprising the step of transferring said digital verbal data from a portable computing device to a second computing device.

19. A method of creating structured information comprising the steps of:
   a. visually displaying data entry influence material on a hand held data entry device;
   b. user generating verbal information which is shaped to at least some degree by said data entry influence material;
   c. capturing at least a portion of said verbal information on said hand held data entry device;
   d. inserting at least some data structure information with at least a portion of said captured verbal information on said hand held data entry device to create composite structured data;
   e. at least temporarily storing said composite structured data on said hand held data entry device.

20. A method of creating structured data as described in claim 19 wherein said step of inserting at least some data structure information with at least a portion of said captured verbal information on said hand held data entry device to create composite structured data comprises the step of inserting partial data structure information to create composite structured data.

21. A method of creating structured data as described in claim 20 and further comprising the step of transferring said composite structured data from said hand held data entry device to a full featured computing device.

22. A method of creating structured data as described in claim 19 wherein said step of capturing at least a portion of said verbal information on said hand held data entry device comprises the step of generating a wave file on said hand held data entry device.

23. A method of creating structured data as described in claim 21 and further comprising the step of transforming digital verbal data into structured data within a data context at said full featured computing device.

24. A method of creating structured data as described in claim 21 wherein said step of transferring said composite structured data from said hand held data entry device comprises the step of transferring said composite structured data in manner selected from a group consisting of a wireless manner of transfer, an internet manner of transfer, and a cellular telephone system based manner of transfer.

25. A structured information creation system comprising:
   a. a stored data context element;
   b. a visual display responsive to said stored data context element;
   c. a verbal information entry element which accepts the entry of verbal information;
   d. a file generation element responsive to said verbal information entry element;
   e. a verbal information memory element responsive to said file generation element;
   f. a data context configured structured data establishment element responsive to said verbal information memory configured to the creation of structured data within said data context based upon said verbal information and converted to digital data, and that includes at least some data in a meta language format; and
   g. a structured data memory responsive to said structured data establishment element, and wherein said stored data context element comprises an element related to a context selected from a group consisting of: data input need context, a data information need context, a user reminder context, a currency of information context, a statistical input need context, and a near real time statistical generated need context.

26. A structured information creation system as described in claim 25 wherein said visual display is controlled by a computing device, and wherein said file generation element is controlled by said same computing device.

27. A structured information creation system as described in claim 26 wherein said computing device comprises a hand held data entry device.

28. A structured information creation system as described in claim 27 and further comprising a data transfer element to which a second computing device is responsive.

29. A structured information creation system as described in claim 28 wherein said data transfer element comprises a data transfer element selected from a group consisting of wireless transfer element, an internet transfer element, and a cellular telephone system transfer element.

30. A structured information creation system comprising:
   a. a stored data context element;
   b. a verbal information entry element which accepts the entry of verbal information;
   c. a verbal information memory responsive to said verbal information entry element;
   d. a data context configured tagged structured data establishment element responsive to said verbal information memory and configured to the creation of structured data within said data context based upon said verbal information, and converted to digital data, and that includes at least some data in a meta language format; and
   e. a structured data memory responsive to said structured data establishment element, and wherein said stored data context element comprises an element related to a context selected from a group consisting of: data input need context, a data information need context, a user reminder context, a currency of information context, a statistical input need context, and a near real time statistical generated need context.

31. A structured information creation system as described in claim 30 and further comprising a file generation element responsive to said verbal information entry element.

32. A structured information creation system as described in claim 31 wherein said data context configured tagged structured data establishment element comprises an unaltered verbal information storage element.

33. A structured information creation system as described in claim 30 wherein said file generation element is controlled at least in part by a first computing device and wherein said data context configured tagged structured data establishment element comprises a transcriptionist input controlled at least in part by a second computing device.

34. A structured information creation system as described in claim 30 and further comprising a visual display responsive to said stored data context element.

35. A structured information creation system as described in claim 34 wherein said visual display responsive to said stored data context element comprises a data entry influence material display at a first computing device, wherein said data context configured tagged structure data establishment element comprises a structured data establishment element at a second computing device.

36. A structured information creation system as described in claim 31 and further comprising:
   a. a data entry influence material display controlled by a first computing device; and
   b. a file generation element responsive to said verbal information entry element and controlled by said same first computing device,
and wherein said data context configured tagged structure data establishment element comprises a structured data establishment element controlled by a second computing device.

37. A structured information creation system as described in claim 36 wherein said first computing device comprises a hand held data entry device.

38. A structured information creation system as described in claim 37 and further comprising a data transfer element to which a second computing device is responsive.

39. A method of creating structured data as described in claim 5 or 11 wherein said step of converting at least a portion of said verbal information into digital verbal data representative of at least a portion of said verbal information comprises the step of generating a wave file.

40. A method of creating structured data as described in claim 4 or 11 wherein said step of transforming said digital verbal data into structured data within said data context comprises the step of ordering said verbal data within said data context.

41. A method of creating structured data as described in claim 4 wherein said step of transforming said digital verbal data into structured data within said data context comprises the step of establishing tagged structured data within said data context.

42. A method of creating structured data as described in claim 4 and further comprising the step of establishing structured data in a tagged format.

43. A method of creating structured data as described in claim 42 or 11 wherein said step of establishing structured data in a tagged format comprises the step of establishing structured data in a format selected from a group consisting of: a field format, an ordered format, a subcontext format, a meta language format, an embedded code format.

44. A method of creating structured data as described in claim 4, 10, 19, or 42 and further comprising the step of accepting binary user input as part of said data creation process.

45. A method of creating structured data as described in claim 4, 14, or 19 wherein said step of visually displaying data entry influence material comprises the step of visually displaying checklist material.

46. A method of creating structured data as described in claim 4, 11, or 23 wherein said step of transforming digital verbal data into structured data within a data context comprises the step of creating multiple structured data formats.

47. A method of creating structured data as described in claim 4, 11, or 23 wherein said step of transforming digital verbal data into structured data within a data context comprises the step of transcribing verbal information.

48. A method of creating structured data as described in claim 47 wherein said step of transcribing verbal information comprises the step of allowing transcriptionist input.

49. A method of creating structured data as described in claim 47 wherein said step of transcribing verbal information comprises the step of establishing structured data in a tagged format.

50. A method of creating structured data as described in claim 49 wherein said step of establishing structured data in a tagged format comprises the step of establishing structured data in an extensible markup language format.

51. A method of creating structured data as described in claim 49 wherein said step of establishing structured data in a tagged format comprises the step of sequencing through data fields.

52. A method of creating structured data as described in claim 4 or 10 wherein said step of establishing a data context comprises the step of establishing a context selected from a group consisting of: data input need context, a data information need context, a user reminder context, a currency of information context, a statistical input need context, and a near real time statistical generated need context.

53. A method of creating structured data as described in claim 4 or 10 wherein said step of establishing a data context comprises the step of creating a document type definition structure.

54. A method of creating structured data as described in claim 4 or 14 wherein said step of establishing a data context comprises the step of creating a document type definition structure, and wherein said step of visually displaying information comprises the step of prompting the generation of data which meets said document type definition structure.

55. A method of creating structured data as described in claim 4, 14, or 19 wherein said step of visually displaying information comprises the step of displaying field segmented information.

56. A method of creating structured data as described in claim 55 wherein said step of displaying field segmented information comprises the step of sequencing through field segmented information.

57. A method of creating structured data as described in claim 4, 10, or 23 and further comprising the step of statistically analyzing said data.

58. A method of creating structured data as described in claim 4, 10, or 23 and further comprising the steps of:
   a. aggregating multiple stored structured data into a database; and
   b. analyzing said database for aggregate information.

59. A method of creating structured data as described in claim 58 wherein said step of analyzing said database for aggregate information comprises the step of analyzing said database by use of a process selected from a group consisting of: statistical analysis, trend analysis, artificial intelligence analysis, and neural network analysis.

60. A method of creating structured data as described in claim 9, 10, or 23 and further comprising the steps of:
   a. analyzing said structured data;
   b. identifying relevant information as a result of said analysis; and
   c. providing said relevant information to a user.

61. A method of creating structured data as described in claim 60 wherein said step of providing said relevant information to a user comprises a step selected from a group consisting of: providing retroactive information, uploading information to said user, alerting said user to a particular concern, querying said user for additional information, and informing said user of available information.

62. A method of creating structured data as described in claim 57 wherein said step of statistically analyzing said data comprises the step of correlating events by location.

63. A method of creating structured data as described in claim 62 wherein said step of correlating events by location comprises the step of correlating battlefield events.

64. A method of creating structured data as described in claim 62 wherein said step of correlating events by location comprises the step of correlating event within a location selected from a group consisting of: a town, a county, a postal chain, multiple postal chains, a governmental subdivision, and a pre-established statistical area.

65. A method of creating structured data as described in claim 4, 10, or 19 and further comprising the step of providing information to a central authority.

66. A method of creating structured data as described in claim 65 wherein said step of providing information to a central authority comprises the step of automatically providing information to an authority selected from a group consisting of: the Center for Disease Control, the Office of Homeland Security, a law enforcement agency, and multiple law enforcement agencies.

67. A method of creating structured data as described in claim 4, 10, or 19 and further comprising the step of displaying relevant information to said user.

68. A method of creating structured data as described in claim 67 wherein said step of displaying relevant information to said user comprises the step of displaying information selected from a group consisting of: healthcare provider alert information, symptom identification information, location specific information, and entry prompt information.

69. A method of creating structured data as described in claim 4, 14, or 19 and further comprising the step of uploading information to said user.

70. A method of creating structured data as described in claim 69 and further comprising the steps of:
   a. analyzing said structured data; and
   b. identifying relevant information as a result of said analysis;
and wherein said step of uploading information to said user comprises the step of providing said relevant information to a user.

71. A method of creating structured data as described in claim 69 wherein said step of uploading information to said user comprises the step of updating information prior to said step of user generating verbal information.

72. A method of creating structured data as described in claim 71 wherein said step of updating information prior to said step of user generating verbal information comprises the step of updating information at the time of a prior download of information.

73. A method of creating structured data as described in claim 71 wherein said step of providing said relevant information to a user comprises the step of alerting said user to an important healthcare concern.

74. A method of creating structured data as described in claim 4, 10, or 19 wherein said step of user generating verbal information comprises the step of generating medical diagnosis information.

75. A method of creating structured data as described in claim 74 wherein said step of generating medical diagnosis information comprises the step of dictating patient diagnosis information.

76. A method of creating structured data as described in claim 74 wherein said step of generating medical diagnosis information comprises the step of dictating insurance claim information.

77. A method of creating structured data as described in claim 74 wherein said step of generating medical diagnosis information comprises the step of dictating potentially exotic medical event information.

78. A method of creating structured data as described in claim 74 wherein said step of generating medical diagnosis information comprises the step of dictating potential bioweapon symptom information.

79. A method of creating structured data as described in claim 74 wherein said step of generating medical diagnosis information comprises the step of dictating Centers for Medicare and Medicaid Services secure information.

80. A method of creating structured data as described in claim 79 and further comprising the step of securely transferring said Centers for Medicare and Medicaid Service secure information.

81. A method of creating structured data as described in claim 74 and further comprising the steps of:
   a. stripping individual identity information to create individual anonymous information; and
   b. providing said individual anonymous information.

82. A method of creating structured data as described in claim 4, 10, or 19 wherein said step of user generating verbal information comprises the step of generating law enforcement related information.

83. A method of creating structured data as described in claim 82 wherein said step of generating law enforcement related information comprises the step of dictating crime scene information.

84. A method of creating structured data as described in claim 82 wherein said step of generating law enforcement related information comprises the step of dictating potential terrorist event information.

85. A method of creating structured data as described in claim 82 wherein said step of generating law enforcement related information comprises the step of dictating potential bioweapon event information.

86. A method of creating structured data as described in claim 82 wherein said step of generating law enforcement related information comprises the step of dictating accident event information.

87. A method of creating structured data as described in claim 19 wherein said step of user generating verbal information comprises the step of generating business information.

88. A method of creating structured data as described in claim 4, 10, or 87 wherein said step of generating business information comprises the step of dictating business billing information.

89. A method of creating structured data as described in claim 4, 10, or 87 wherein said step of generating business information comprises the step of dictating service provided information.

90. A structured information creation system as described in claim 23, or 31 wherein said file generation element comprises a wave file generator.

91. A structured information creation system as described in claim 25 or 31 wherein said data context configured structured data establishment element comprises an entry order element.

92. A structured information creation system as described in claim 25 wherein said data context configured structured data establishment element comprises a data context configured tagged structured data establishment element.

93. A structured information creation system as described in claim 25 and further comprising a data context configured tagged structured data establishment element.

94. A structured information creation system as described in claim 93 or 34 wherein said data context configured tagged structured data establishment element established a format selected from a group consisting of: a field format, an ordered format, a subcontext format, a meta language format, an embedded code format.

95. A structured information creation system as described in claim 25 or 93 and further comprising a binary user input element.

96. A structured information creation system as described in claim 25 or 34 wherein said visual display comprises a checklist display.

97. A structured information creation system as described in claim 25 or 31 wherein said data context configured structured data establishment element comprises a multiple data structure establishment element.

98. A structured information creation system as described in claim 25 or 31 wherein said data context configured structured data establishment element comprises an inserted code transcription system.

99. A structured information creation system as described in claim 98 wherein said inserted code transcription system comprises a transcriptionist input element.

100. A structured information creation system as described in claim 99 wherein said inserted code transcription system further comprises a tagged data input.

101. A structured information creation system as described in claim 100 wherein said inserted code transcription system further comprises an extensible markup language generator.

102. A structured information creation system as described in claim 100 wherein said tagged data input comprises a sequenced field element.

103. A structured information creation system as described in claim 25 or 30 wherein said stored data context element comprises a document type definition structure element.

104. A structured information creation system as described in claim 25 or 34 wherein said stored data context element comprises a document type definition structure element, and wherein said visual display element comprises a document type definition structure prompt.

105. A structured information creation system as described in claim 25 or 34 wherein said visual display comprises a field segmented display.

106. A structured information creation system as described in claim 25 or 30 and further comprising a statistical analysis element.

107. A structured information creation system as described in claim 25 or 30 and further comprising an aggregated multiple stored structured data analysis element.

108. A structured information creation system as described in claim 107 wherein said aggregated multiple stored structured data analysis element comprises an element selected from a group consisting of: statistical analysis element, a trend analysis element, an artificial intelligence analysis element, and a neural network analysis element.

109. A structured information creation system as described in claim 25 or 30 and further comprising:
  a. a data analysis element;
  b. a relevant information identification element responsive to said data analysis element; and
  c. a relevant information display responsive to said relevant information identification element.

110. A structured information creation system as described in claim 109 wherein said relevant information identification element comprises an element selected from a group consisting of: a retroactive information element, an information upload element, an information alert element, an information query element, and an information availability element.

111. A structured information creation system as described in claim 106 wherein said statistical analysis element comprises a locational event correlation element.

112. A structured information creation system as described in claim 111 wherein said locational event correlation element comprises a battlefield correlation element.

113. A structured information creation system as described in claim 111 wherein said locational event correlation element comprises an element selected from a group consisting of: a town-wide event correlation element, a county-wide event correlation element, a postal chain-wide event correlation element, a multiple postal chain-wide event correlation element, a governmental subdivision-wide event correlation element, and a pre-established statistical area-wide event correlation element.

114. A structured information creation system as described in claim 25 or 30 further comprising a central authority download element.

115. A structured information creation system as described in claim 114 wherein said central auth download element comprises an authority download element selected from a group consisting of: a Center for Disease Control download element, a Office of Homeland Security download element, a law enforcement agency download element, and multiple law enforcement agency download element.

116. A structured information creation system as described in claim 25 or 34 and further comprising an information upload element.

117. A structured information creation system as described in claim 116 and further comprising a data analysis element and wherein said information upload element is responsive to said data analysis element.

118. A structured information creation system as described in claim 116 wherein said information upload element comprises a pre-utilization information upload element.

119. A structured information creation system as described in claim 118 wherein said pre-utilization information upload element comprises a download linked information upload element.

120. A structured information creation system as described in claim 117 and further comprising a user alert element.

121. A structured information creation system as described in claim 25 or 30 wherein said stored data context element comprises a medical diagnosis information element.

122. A structured information creation system as described in claim 121 wherein said medical diagnosis information element comprises a patient diagnosis information element.

123. A structured information creation system as described in claim 121 wherein said medical diagnosis information element comprises an medical insurance information element.

124. A structured information creation system as described in claim 121 wherein said medical diagnosis information element comprises an exotic medical event information element.

125. A structured information creation system as described in claim 121 wherein said medical diagnosis information element comprises a bioweapon diagnosis information element.

126. A structured information creation system as described in claim 121 and further comprising a Centers for Medicare and Medicaid Service secure information transfer element.

127. A structured information creation system as described in claim 121 and further comprising an individual identity information stripper.

128. A structured information creation system as described in claim 25 or 30 wherein said stored data context element comprises a law enforcement information element.

129. A structured information creation system as described in claim 128 wherein said law enforcement information element comprises a crime scene information element.

130. A structured information creation system as described in claim 128 wherein said law enforcement information element comprises a potential terrorist event information element.

131. A structured information creation system as described in claim 128 wherein said law enforcement information element comprises a potential bioweapon event information element.

132. A structured information creation system as described in claim 128 wherein said law enforcement information element comprises an accident investigation information element.

133. A structured information creation system as described in claim 25 or 30 wherein said stored data context element comprises a business information element.

134. A structured information creation system as described in claim 133 wherein said business information element comprises a billing information element.

135. A structured information creation system as described in claim 133 wherein said business information element comprises a services provided information element.

136. A structured information creation system comprising:
   a. a stored data context element;
   b. a visual display responsive to said stored data context element;
   c. a verbal information entry element which accepts the entry of verbal information;
   d. a file generation element responsive to said verbal information entry element;
   e. a verbal information memory element responsive to said file generation element;
   f. a data context configured structured data establishment element responsive to said verbal information memory configured to the creation of structured data within said data context based upon said verbal information, and converted to digital data, and that includes at least some data in a meta language format;
   g. a structured data memory responsive to said structured data establishment element; and
   h. a relevant information display selected from a group consisting of: a healthcare provider alert information display, a symptom identification information display, a location specific information display, and an entry prompt information display.

137. A structured information creation system as described in claim 136 wherein said visual display is controlled by a computing device, and wherein said file generation element is controlled by said same computing device.

138. A structured information creation system as described in claim 137 wherein said computing device comprises a hand held data entry device.

139. A structured information creation system as described in claim 138 and further comprising a data transfer element to which a second computing device is responsive.

140. A structured information creation system as described in claim 139 wherein said data transfer element comprises a data transfer element selected from a group consisting of wireless transfer element, an internet transfer element, and a cellular telephone system transfer element.

141. A structured information creation system comprising:
   a. a stored data context element;
   b. a verbal information entry element which accepts the entry of verbal information;
   c. a verbal information memory responsive to said verbal information entry element;
   d. a data context configured tagged structured data establishment element responsive to said verbal information memory and configured to the creation of structured data within said data context based upon said verbal information, and converted to digital data, and that includes at least some data in a meta language format;
   e. a structured data memory responsive to said structured data establishment element; and
   f. a relevant information display selected from a group consisting of: a healthcare provider alert information display, a symptom identification information display, a location specific information display, and an entry prompt information display.

142. A structured information creation system as described in claim 141 and further comprising a file generation element responsive to said verbal information entry element.

143. A structured information creation system as described in claim 142 wherein said data context configured tagged structured data establishment element comprises an unaltered verbal information storage element.

144. A structured information creation system as described in claim 143 wherein said file generation element is controlled at least in part by a first computing device and wherein said data context configured tagged structured data establishment element comprises a transcriptionist input controlled at least in part by a second computing device.

145. A structured information creation system as described in claim 141 and further comprising a visual display responsive to said stored data context element.

146. A structured information creation system as described in claim 145 wherein said visual display responsive to said stored data context element comprises a data entry influence material display at a first computing device, wherein said data context configured tagged structure data establishment element comprises a structured data establishment element at a second computing device.

147. A structured information creation system as described in claim 142 and further comprising:
   a. a data entry influence material display controlled by a first computing device; and
   b. a file generation element responsive to said verbal information entry element and controlled by said same first computing device,
and wherein said data context configured tagged structure data establishment element comprises a structured data establishment element controlled by a second computing device.

148. A structured information creation system as described in claim 147 wherein said first computing device comprises a hand held data entry device.

149. A structured information creation system as described in claim 148 and further comprising a data transfer element to which a second computing device is responsive.

150. A structured information creation system as described in claim 136 or 142 wherein said file generation element comprises a wave file generator.

151. A structured information creation system as described in claim 136 or 141 wherein said data context configured structured dataestablishment element comprises an entry order element.

152. A structured information creation system as described in claim 136 wherein said data context configured structured data establishment element comprises a data context configured tagged structured data establishment element.

153. A structured information creation system as described in claim 136 and further comprising a data context configured tagged structured data establishment element.

154. A structured information creation system as described in claim 141 or 153 wherein said data context configured tagged structured data establishment element established a format selected from a group consisting of: a field format, an ordered format, a subcontext format, a meta language format, an embedded code format.

155. A structured information creation system as described in claim 136 or 153 and further comprising a binary user input element.

156. A structured information creation system as described in claim 136 wherein said visual display comprises a checklist display.

157. A structured information creation system as described in claim 136 or 141 wherein said data context configured structured data establishment element comprises a multiple data structure establishment element.

158. A structured information creation system as described in claim 136 or 141 wherein said data context configured structured data establishment element comprises an inserted code transcription system.

159. A structured information creation system as described in claim 158 wherein said inserted code transcription system comprises a transcriptionist input element.

160. A structured information creation system as described in claim 159 wherein said inserted code transcription system further comprises a tagged data input.

161. A structured information creation system as described in claim 160 wherein said inserted code transcription system further comprises an extensible markup language generator.

162. A structured information creation system as described in claim 160 wherein said tagged data input comprises a sequenced field element.

163. A structured information creation system as described in claim 136 or 141 wherein said stored data context element comprises an element related to a context selected from a group consisting of: data input need context, a data information need context, a user reminder context, a currency of information context, a statistical input need context, and a near real time statistical generated need context.

164. A structured information creation system as described in claim 136 or 141 wherein said stored data context element comprises a document type definition structure element.

165. A structured information creation system as described in claim 136 wherein said stored data context element comprises a document type definition structure element, and wherein said visual display element comprises a document type definition structure prompt.

166. A structured information creation system as described in claim 136 wherein said visual display comprises a field segmented display.

167. A structured information creation system as described in claim 136 or 141 and further comprising a statistical analysis element.

168. A structured information creation system as described in claim 136 or 141 and further comprising an aggregated multiple stored structured data analysis element.

169. A structured information creation system as described in claim 168 wherein said aggregated multiple stored structured data analysis element comprises an element selected from a group consisting of: statistical analysis element, a trend analysis element, an artificial intelligence analysis element, and a neural network analysis element.

170. A structured information creation system as described in claim 136 or 141 and further comprising:
   a. a data analysis element;
   b. a relevant information identification element responsive to said data analysis element; and
   c. a relevant information display responsive to said relevant information identification element.

171. A structured information creation system as described in claim 170 wherein said relevant information identification element comprises an element selected from a group consisting of: a retroactive information element, an information upload element, an information alert element, an information query element, and an information availability element.

172. A structured information creation system as described in claim 167 wherein said statistical analysis element comprises a locational event correlation element.

173. A structured information creation system as described in claim 167 wherein said locational event correlation element comprises a battlefield correlation element.

174. A structured information creation system as described in claim 172 wherein said locational event correlation element comprises an element selected from a group consisting of: a town-wide event correlation element, a county-wide event correlation element, a postal chain-wide event correlation element, a multiple postal chain-wide event correlation element, a governmental subdivision-wide event correlation element, and a pre-established statistical area-wide event correlation element.

175. A structured information creation system as described in claim or 136 or 141 and further comprising a central authority download element.

176. A structured information creation system as described in claim 173 wherein said central auth download element comprises an authority download element selected from a group consisting of: a Center for Disease Control download element, a Office of Homeland Security download element, a law enforcement agency download element, and multiple law enforcement agency download element.

177. A structured information creation system as described in claim 136 and further comprising an information upload element.

178. A structured information creation system as described in claim 177 and further comprising a data analysis element and wherein said information upload element is responsive to said data analysis element.

179. A structured information creation system as described in claim 177 wherein said information upload element comprises a pre-utilization information upload element.

180. A structured information creation system as described in claim 179 wherein said pre-utilization information upload element comprises a download linked information upload element.

181. A structured information creation system as described in claim 178 and further comprising a user alert element.

182. A structured information creation system as described in claim 136 or 141 wherein said stored data context element comprises a medical diagnosis information element.

183. A structured information creation system as described in claim 182 wherein said medical diagnosis information element comprises a patient diagnosis information element.

184. A structured information creation system as described in claim 182 wherein said medical diagnosis information element comprises an medical insurance information element.

185. A structured information creation system as described in claim 182 wherein said medical diagnosis information element comprises an exotic medical event information element.

186. A structured information creation system as described in claim 182 wherein said medical diagnosis information element comprises a bioweapon diagnosis information element.

187. A structured information creation system as described in claim 182 and further comprising a Centers for Medicare and Medicaid Service secure information transfer element.

188. A structured information creation system as described in claim 182 and further comprising an individual identity information stripper.

189. A structured information creation system as described in claim 136 or 141 wherein said stored data context element comprises a law enforcement information element.

190. A structured information creation system as described in claim 189 wherein said law enforcement information element comprises a crime scene information element.

191. A structured information creation system as described in claim 189 wherein said law enforcement information element comprises a potential terrorist event information element.

192. A structured information creation system as described in claim 189 wherein said law enforcement information element comprises a potential bioweapon event information element.

193. A structured information creation system as described in claim 189 wherein said law enforcement information element comprises an accident investigation information element.

194. A structured information creation system as described in claim 136 or 141 wherein said stored data context element comprises a business information element.

195. A structured information creation system as described in claim 194 wherein said business information element comprises a billing information element.

196. A structured information creation system as described in claim 194 wherein said business information element comprises a services provided information element.

* * * * *